United States Patent [19]
Cipkowski

[11] Patent Number: 5,976,895
[45] Date of Patent: Nov. 2, 1999

[54] DEVICE FOR THE COLLECTION, TESTING AND SHIPMENT OF BODY FLUID SAMPLES

[75] Inventor: Stan Cipkowski, Ancramdale, N.Y.

[73] Assignee: American BioMedica Corporation, Hudson, N.Y.

[21] Appl. No.: 08/613,487

[22] Filed: Mar. 11, 1996

[51] Int. Cl.[6] .......................... G01N 33/543; G01N 33/94
[52] U.S. Cl. .......................... 436/518; 422/58; 422/68.1; 422/102; 435/7.1; 435/7.93; 435/7.94; 435/287.2; 435/288.7; 435/970; 435/975; 436/525; 436/164; 436/169; 436/816; 436/901; 600/584
[58] Field of Search .................................. 436/514, 518, 436/525, 810, 816, 901; 422/55, 56, 57, 58, 68.1, 102; 435/7.1, 7.93, 7.94, 970, 287.2, 973, 288.4, 288.7, 975; 128/771; 600/574, 584

[56] References Cited

U.S. PATENT DOCUMENTS

| | | | |
|---|---|---|---|
| 3,900,019 | 8/1975 | Logiadis | 600/574 |
| 4,225,557 | 9/1980 | Hartl et al. | 422/58 |
| 4,361,537 | 11/1982 | Deutsch et al. | 422/56 |
| 4,518,565 | 5/1985 | Boger et al. | 422/58 |
| 4,822,565 | 4/1989 | Kohler | 422/57 |
| 5,119,830 | 6/1992 | Davis | 600/584 |
| 5,238,652 | 8/1993 | Sun et al. | 422/58 |
| 5,403,551 | 4/1995 | Galloway et al. | 422/58 |
| 5,441,698 | 8/1995 | Norell | 422/58 |
| 5,500,375 | 3/1996 | Lee-Owen et al. | 436/518 |
| 5,712,172 | 1/1998 | Huang et al. | 436/518 |

*Primary Examiner*—James C. Housel
*Assistant Examiner*—James L. Grun
*Attorney, Agent, or Firm*—Edmund M. Jaskiewicz

[57] ABSTRACT

A drug abuse test kit has a transparent cup-like container for retaining a fluid sample to be tested and the open top end of the container is closed by an inner closure insert seated within the open end. There is a slit in the inner closure insert to receive a multiple drug test card having a plurality of immunoassay test strips thereon with visual endpoints to indicate presence or absence of a particular drug. The container is provided with an outer cover to close and seal the container when a sample therein is to be transported.

6 Claims, 5 Drawing Sheets

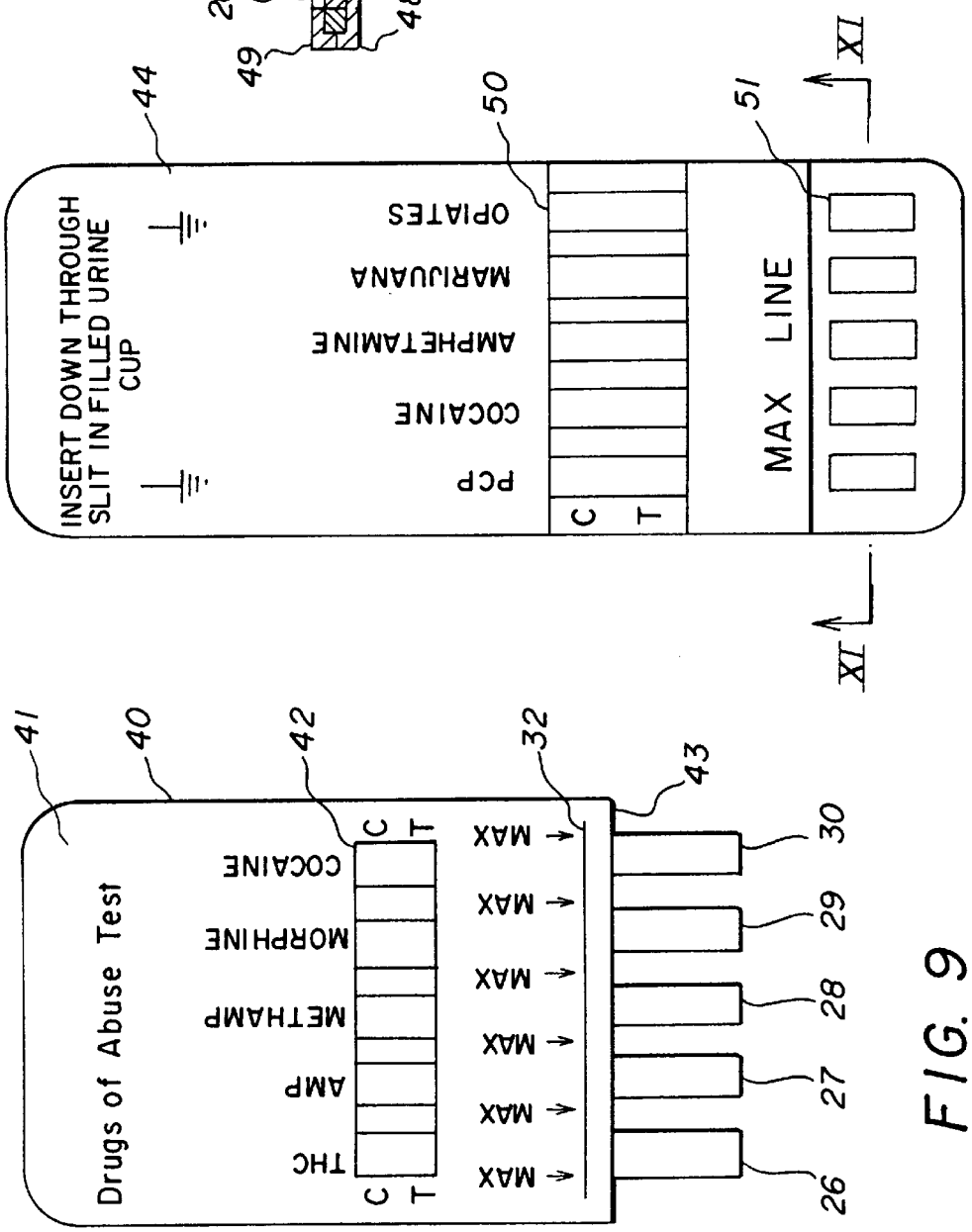

DEVICE FOR THE COLLECTION, TESTING AND SHIPMENT OF BODY FLUID SAMPLES

The present invention relates to a test kit for the collection and testing of urine samples for drugs of abuse and subsequent shipment of the sample, more particularly, to such a test kit having a cup-like container and a test card for indicating visually the presence of particular drugs of abuse.

The increased availability and use of drugs of abuse by the general population has caused employers, governmental agencies, sports groups and other organizations to utilize drug screening both as a condition of employment and in order to maintain safety in the work place. Typical drug screening tests are performed for the purpose of quickly identifying on a qualitative basis the presence of drugs in a body fluid which may be urine. A complete analysis of the sample may then be carried out in a laboratory only if the preliminary screening results are positive. More and more such drug screenings are taking place on site or the work place and are generally carried out by testing personnel who are generally not technically trained, such as laboratory technicians. It is thus important that the drug screening procedure is simple but yet reliable. Further, the test apparatus must be such so as to enable the testing personnel to avoid all contact with the fluid specimen which is being tested.

Various forms of devices have been proposed for the collection and taking of body fluids, such as urine, which have provided to be cumbersome in operation since they involve a number of separate steps. Initially, the sample was collected and several additional steps were then required to transfer the urine sample to an analysis device. This multiple step procedure required the manual handling of the specimen through various devices and the use of such transfer devices inevitably caused spills which may result in contamination to the tester and surroundings. In addition, non-technical personnel who perform the screening tests on urine samples objected to coming into any kind of contact with the urine sample and even the handling of the sample itself.

Many of the known testing devices were rather complex in that they included a container for the specimen, and, subsequently it was necessary to transfer the specimen or at least a portion thereof to another compartment of the container in order to perform the test. This transfer of the specimen required vigorous shaking of the container or turning the container upside down in order to cause the flow of the specimen into a test compartment. It was therefore necessary to make the containers leak proof under such condition and the result was a complicated and expensive container structure.

Further, the containers incorporated the structure by means of which reagent strips were mounted in a test compartment of the container and which structure also enabled the fluid sample to flow into the test compartment into contact with the reagent strips. Such a mounting of the reagent strips further resulted in complicating the structure of the container since it was also necessary that provision be made to view the reagent strips from outside of the container. This was generally achieved by providing a transparent window or some other mounting of the reagent strips so as to be visible to testing personnel.

SUMMARY OF THE INVENTION

It is therefore the principal object of the present invention to provide a simplified and inexpensive device for the collection and testing of body fluid samples, particularly urine, for drugs of abuse and subsequent shipment of the sample.

It is an additional object of the present invention to provide such a device which includes a closed container for retaining a urine sample having such a closure structure that a plurality of test strips may be introduced into the container to contact the urine sample.

It is a further object of the present invention to provide a test card having a plurality of immunoassay test strips thereon with each strip being responsive to a particular drug of abuse and having a visual endpoint to indicate the presence or absence of a particular drug.

The objects of the present invention are achieved and the disadvantages of the prior art are eliminated by the drug abuse test device according to the present invention which may comprise a cup-like transparent container for retaining a urine sample to be tested. The open top of the container has an inner closure insert seated therein and there is a diametrical slit in the insert. The slit is of such a size to accommodate a test card which has a plurality of immunoassay test strips mounted thereon in parallel on one side and each test strip is responsive to a particular drug o-F abuse. The test card is insertable through the slit so as to have one end immersed in the urine sample to a predetermined depth whereby the visual results of each test strip can be seen through the transparent wall of the container without removing the test card from the container so as to indicate the presence or absence of a particular drug of abuse in the urine sample. If the sample should test "positive" to indicate the presence of a drug in the urine, it is then necessary to send the sample to a laboratory for confirmatory testing. For this purpose, an outer closure cap is provided which may be threaded onto the open end of the cup-like container. The insert; and the test card are removed from the container, the outer closure cap is threaded on to close the container and the container is then ready for shipment to a laboratory.

As described above, the test kit includes a drug abuse test device for collecting and testing a urine sample. This test device comprises a cup-like container having a transparent wall and having an open top in which is seated an inner closure insert. The surface of the insert is spaced inwardly of the outer end of the container and is provided with a slit therein to receive a test card. An outer closure cap which threads over the outer end of the cup-like container is provided to seal the container to permit the safe shipment of a fluid sample therein.

The test kit also includes a screen test card for drugs of abuse which may comprise a thin flat member having the size and shape of a business card. A plurality of immunoassay test strips are fastened side by side in parallel on one side of the test card within the outline of the card. Each test strip is reactive to provide a visual indication in response to a particular drug of abuse. This test card thus provides for the simultaneous detection of multiple analytes.

BRIEF DESCRIPTION OF THE DRAWINGS

Other objects and advantages of the present invention will be apparent upon reference to the accompanying description when taken in conjunction with the following drawings, which are exemplary, wherein;

FIG. 9 is a plan view of the test side of a modification of the test card.

FIG. 10 is a plan view of the test side of a further modification of the test card;

FIG. 11 is an end elevational view of the test card shown in FIG. 10 viewed from the test end thereof.

DETAILED DESCRIPTION

Proceeding next to the drawings wherein like reference symbols indicate the same parts throughout the various views a specific embodiment and modifications of the present invention will be described in detail.

Figure 1:
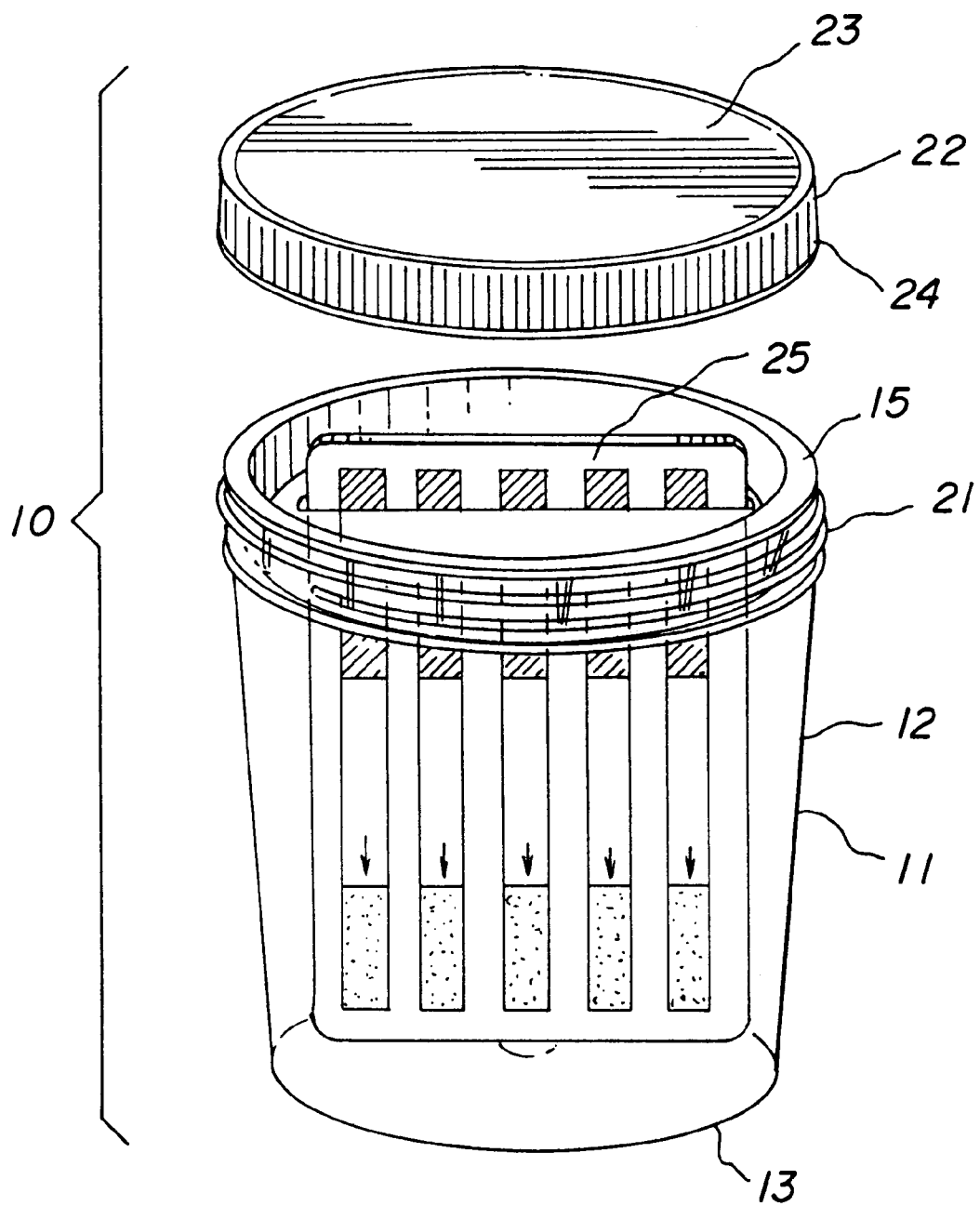
FIG. 1 is an exploded perspective view of the drug abuse test kit according to the present invention generally showing the container, the test card inserted in the testing position in the container and a cover.
Figure 2:
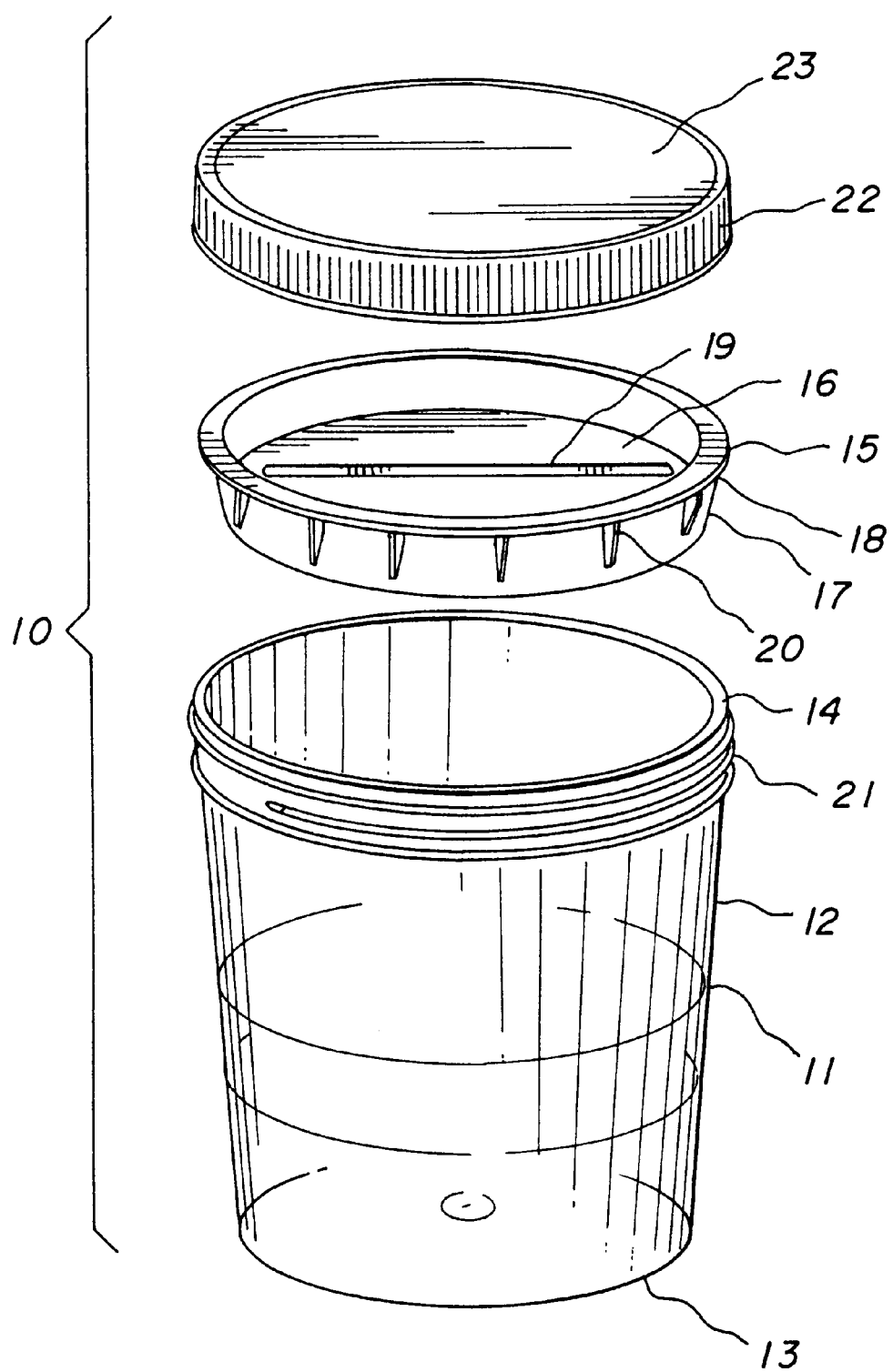
FIG. 2 is an exploded perspective view of the container according to the present invention for collecting and testing a fluid sample and generally showing the container, an inner closure insert and an outer closure cap.
Figure 3:
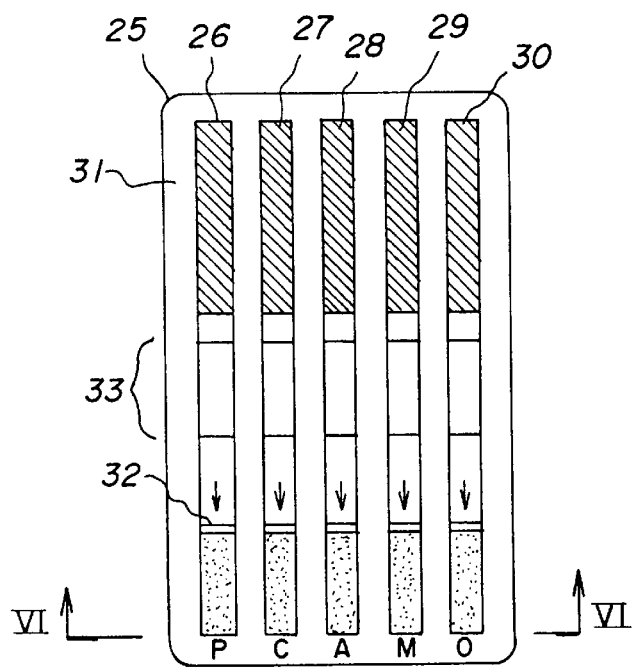
FIG. 3 is a plan view of the test side of the test card according to the present invention.
Figure 4:
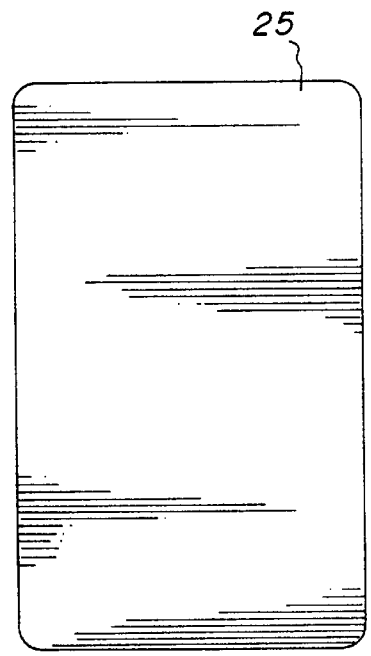
FIG. 4 is a reverse view of the test card shown in FIG. 3.

As may be seen in FIG. 1, a drug abuse test kit according to the present invention is indicated generally at 10 and comprises a cup-like transparent container 11 having a cylindrical side wall 12, a closed bottom 13 and an open top 14. The cylindrical wall 12 may have a slight taper or be straight. The open top end 14 is closed by an inner closure insert 15 which is shown disassembled in FIG. 2. The insert 15 comprises a circular base 16 from the periphery of which there is an upstanding vertical side wall 17 having an outer flange 18 at the top thereof. The flange 18 seats upon the peripheral edge of the cup open end 14 and fixes the position of the insert within the cup. The base 16 of the insert is provided with a substantially diametrical slot 19 which is shaped to accommodate a test card as will be presently described.

On the outer surface of the cylindrical wall 17 there is a plurality of spaced triangular or wedge shaped reinforcing members 20 extending upwardly to the underside of the flange 18. These reinforcing members 20 also facilitate the removal of the insert from the open end of the cup.

The open end 14 of the test cup 11 is provided with external threads 21 upon which is seated an outer closure member or cover 22 provided with corresponding internal threads which are not shown in the drawing. The outer cover 22 comprises a circular top surface 23 from the periphery of which depends a cylindrical wall 24 on the inner surface of which are provided the internal threads.

A test card 25 which will indicate the presence or absence of any one of five different drugs of abuse is shown in FIG. 1 inserted within the slit 19 in the inner closure member 15. The test card is of the multiple drug type in that test strips for five different drugs of abuse are mounted on the test card. The test strips 26–30 are spaced apart in parallel on a test side 31 of the test card. These test strips indicate the presence or absence of the following specific drugs of abuse: PCP (P), cocaine (C), amphetamines (A), marijuana (M) and opiates (0). Test strips 26–30 may be of the type as made by Bionike of South San Francisco, Calif. and Applied Biotech, Inc. of San Diego, Calif. Such test strips are characterized as immunoassay strips and employ colloidal gold chemistry.

Each test strip is submerged up to a maximum line indicated at 32 and the results of the test are read in a test area indicated at 33. A blue line in the test area indicates positive or the presence of the particular drug in the test sample.

Figure 5:
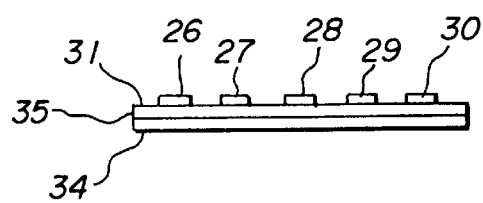
FIG. 5 is an end elevational view of the test card shown in FIG. 3.
Figure 6:
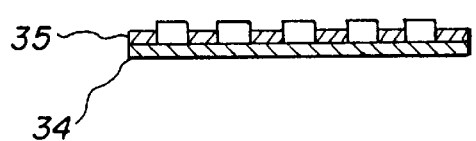
FIG. 6 is a sectional view taken along the lines VI—VI of FIG. 3.
Figure 7:
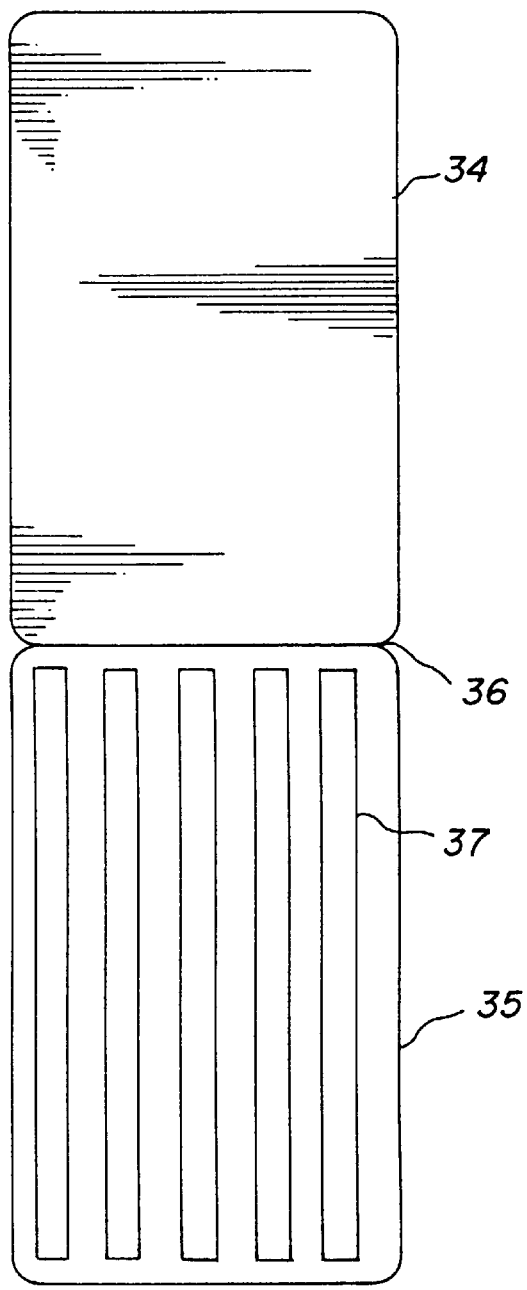
FIG. 7 is a plan view of the opened two piece test card before it is folded over to form the test card shown in FIGS. 3–6.

The test strips are actually recessed in slots in the card so that portions of the test strips project above the test surface 31 of the card as may be seen in FIG. 5. The test card is preferably formed of two plys 34 and 35 as may be seen in FIG. 7 and these plys in turn are formed from a single strip having a bend or fold 36. The ply 35 is formed within a plurality of dye cut slots 37 which are shaped and sized to receive each of the test strips. Thus, in the fabrication of a test card, the two portions 34 and 35 are folded over at end 36 and are adhered together. The test strips are then placed into the slots as shown in FIG. 6 and each of the test strips is adhered to the surface of the first portion 34 upon which the second portion 35 has been folded.

It is also within the scope of this invention to make this test card of two separate or individual plys 34 and 35 which are then adhered together and the strips are fixed in the slots as described above.

In order to conduct a drug abuse test utilizing the test card according to the present invention a person being tested must first provide a urine specimen into the transparent test cup 11. The quantity of specimen provided must be such as to permit insertion of the test card up to about the maximum line indicated at 32. It is also possible to provide fill lines on the wall surface of the test container.

The test cup with a sufficient quantity of test specimen therein is then closed by inserting the inner closure insert 15 within the top of the test cup. The insert is preferably provided with a readily removable adhesive drug strip which is placed over the slit 19. Thus, when the container with the-test specimen is brought to the person conducting the, test, the protective strip is removed and the multiple drug test card 25 inserted into the slit so that the bottom of the test card rests upon the bottom of the test cup in the manner as shown in FIG. 1. 15 ml. of specimen will ensure that the specimen does not go above the maximum fill line 32. The test card then remains in place for at least three minutes and the results of the test can be read on each individual test strip through the transparent wall of the container. Thus, if a blue line appears on any one of the test strips, this indicates positive and the presence of that particular drug of abuse in the test specimen. However, if no such blue line appears then the absence of any of the five drugs of abuse from the specimen is indicated. With such a negative result, the urine sample and the container are discarded.

However, when the results of the test are positive, it is preferable to send the specimen to a laboratory for a confirmatory analysis. In order to shop the sample in the container, the inner closure insert is removed and the cover 22 is threaded down tightly upon the open end of the container.

Figure 8:
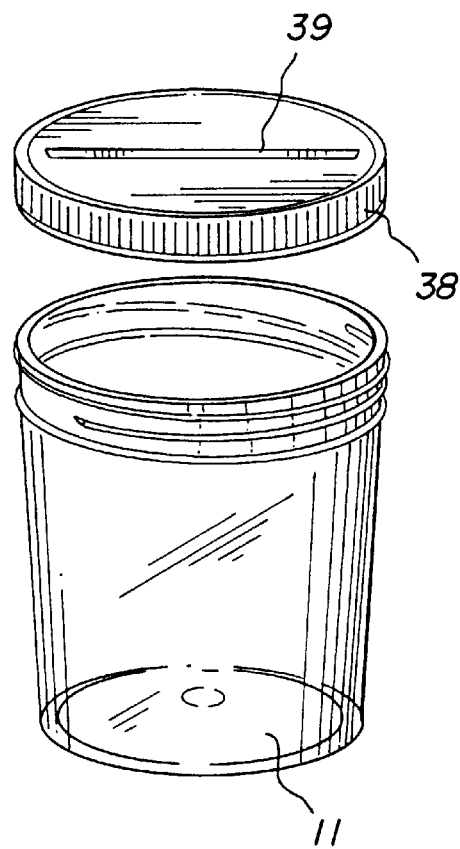
FIG. 8 is an exploded perspective view of a modification of the container according to the present invention in which the inner closure insert is omitted.

As a modification, the inner closure insert 15 may be eliminated completely and an outer cover 38 for the container 11 is provided with a slit 39 through which the multiple drug test card is inserted. Such a modification is shown in FIG. 8. With this modification, if the results of the test are positive and it is contemplated to ship the urine sample to a laboratory for confirmatory testing, the slotted cover is removed and a solid cover such as 22 is. threaded upon the outer end of the container to seal the container against leakage from the fluid specimen therein.

In FIG. 9, there is shown at 40 a modification of the test card as described above and is similarly constructed with two plys but is also provided with a third ply 41 which covers the test stripsas shown in FIG. 9. The third ply 41 is provided with an opening 42 through which the test and control lines may be seen. In this modificiation, those portions of the plys below the maximum fill line 32 are removed such that the test strips 26–30 project beyond the end 43 of the shortened test card. Otherwise, this test card functions in precisely the same manner as described above.

A further modification of the test card is shown at 44 in FIG. 10. In this modification, the test strips are covered but the pertinent test and sample portions of the test strips are exposed through openings. The test card 44 comprises a central ply 45 which has a thickness corresponding to the thickness of the test strips and slots are provided in the center ply to receive the test strips. The top and bottom faces of the central ply 45 are covered by a bottom ply 46 and a top ply 47 which are preferably made from a single piece of material double scored at 48 and 49 so as to wrap around the central ply 45 in the manner as shown in FIG. 11. The top ply 47 is provided with a plurality of test windows 50 through which the test results as indicated by the test strips can be seen. At the lower end of the card are provided sample openings 51 through which the test specimen is able to contact the absorbent or sample portions of the test strips.

The test card 44 functions in the same manner as the previously described test cards in that the card is inserted into the specimen up to the fill line indicated by the wording "max line". The test results are then read through the test windows 50.

The test strips are such that if a single band appears in the control zone and no band appears in the test zone then the results are "positive" which indicates that that particular drug is present above a predetermined level which is usually around 50 ng/ml. If two color bands appear, one in the control region and the other in the test region then the test results are "negative" which indicates that the level of that particular drug is below the predetermined detection of sensitivity.

In the event that there are no distinct color bands visible in both the test zone and the control zone or if there is a visible band in the test zone but not in the control zone, then the result is invalid and retesting of the specimen is recommended with another test card.

As described above, the test card 44 of FIG. 10 may be made of a suitable cardboard or a plastic material.

Thus it can be seen that the present invention discloses a novel and improved drug abuse test kit which comprises a container for the fluid specimen being tested and a multiple drug test card which is inserted in the specimen within the container and the visual results of the test are read on the test card through the transparent wall of the container. The test card thus comprises a number of individual test strips of the immunoassay type and each strip is responsive or indicative to a particular drug of abuse. The test card may be made of plastic coated cardboard or thin sheets of plastic which are laminated together.

It will be understood that this invention is susceptible to modification in order to adapt it to different usages and conditions, and accordingly, it is desired to comprehend such modifications within this invention as may fall within the scope of the appended claims.

What is claimed is:

1. A test kit for testing of fluid samples for drugs of abuse comprising:
   a cup-like substantially transparent container having an open top end for retaining a fluid sample to be tested,
   a closure cap positionable over the open top end of the container to substantially seal the container, said closure cap having a slit therein, and
   a drug of abuse immuno assay test card comprising
      a thin flat member having a rectangular outline and having front and rear surfaces, said thin flat member having a longitudinal dimension extending between top and bottom ends defining a length and having a width less than said length, and being shaped to be insertable into said container longitudinally through said slit when said cap is positioned over the top end of the container,
      one or more immuno assay test strips, each having thereon immunoassay means to visually indicate presence or absence of a selected drug of abuse, disposed longitudinally side-by-side in parallel within said thin flat member and enclosed between said front and rear surfaces,
      each said one or more test strips having a bottom end defining a sample receiving portion and further having a test portion spaced longitudinally therefrom wherein, in use, the presence or absence of the selected drug of abuse in the fluid sample is visually indicated, the bottom end of each said one or more test strips being disposed at the bottom end of said thin flat member but spaced from the bottom end of said thin flat member, the top end of each said one or more test strips being spaced from the top end of said thin flat member,
      said front surface of said thin flat member having a plurality of openings therein to register with and expose each of the sample receiving and test portions of each of said one or more test strips.

2. The test kit as claimed in claim 1, further comprising a protective sealing strip over said slit which is removable prior to testing a fluid sample within said container.

3. The test kit as claimed in claim 1 wherein said slit is diametrically disposed in said closure cap.

4. The test kit as claimed in claim 1, further comprising means within said thin flat member between said front and rear surfaces for defining one or more longitudinally extending slots to longitudinally dispose said one or more test strips, each said one or more slots having both ends closed and spaced from the respective top and bottom ends of said thin flat member, and
   said one or more immuno assay test strips each seated within a respective slot.

5. The test kit as claimed in claim 1 wherein said thin flat member comprises a central ply having a first thickness sandwiched between a top ply defining said front surface and a bottom ply defining said rear surface,
   there being a plurality of side-by-side parallel longitudinally extending slots in said central ply to longitudinally dispose said test strips, said slots having both ends thereof closed and spaced from the respective top and bottom ends of said thin flat member, and
   said immuno assay test strips each seated within a respective slot.

6. The test kit as claimed in claim 1 and further comprising a second closure cap which is solid and positionable over the open end of the container to substantially seal the container.

* * * * *